United States Patent
Koiteh

(10) Patent No.: US 8,449,895 B1
(45) Date of Patent: May 28, 2013

(54) CONDITIONING CLEANSING CREAM

(76) Inventor: Zahraa Koiteh, Bronx, NY (US)

( * ) Notice: Subject to any disclaimer, the term of this patent is extended or adjusted under 35 U.S.C. 154(b) by 113 days.

(21) Appl. No.: 13/135,168

(22) Filed: Jun. 28, 2011

(51) Int. Cl.
*A61K 8/00* (2006.01)
*A61K 8/02* (2006.01)

(52) U.S. Cl.
USPC .......................................... 424/400; 424/401

(58) Field of Classification Search
None
See application file for complete search history.

(56) References Cited

U.S. PATENT DOCUMENTS

| | | | |
|---|---|---|---|
| 6,664,217 B1 * | 12/2003 | Puvvada et al. | 510/141 |
| 2002/0119174 A1 * | 8/2002 | Gardlik et al. | 424/401 |
| 2005/0008663 A1 * | 1/2005 | Lerma | 424/401 |

OTHER PUBLICATIONS

"What is Black Soap?" by Kristin Underwood from www.treehugger.com, Sep. 4, 2008 (accessed Dec. 4, 2012).*

* cited by examiner

*Primary Examiner* — Nissa Westerberg
(74) *Attorney, Agent, or Firm* — Emery L. Tracy

(57) ABSTRACT

A conditioning cleansing cream for removing oil and debris from the hair while leaving it soft, detangled, and conditioned is provided. The conditioning cleansing cream comprises an amount of African Black Soap, an amount of Castor Oil, an amount of Aloe Vera Extract, an amount of Jojoba Oil, an amount of Coconut Oil, an amount of Rosemary extract, an amount of Shea Butter, and an amount of Glycerin.

9 Claims, No Drawings

CONDITIONING CLEANSING CREAM

BACKGROUND OF THE INVENTION

1. Field of the Invention

This invention relates generally to a conditioning cleansing cream and, more particularly, the invention relates to a conditioning cleansing cream for removing oil and debris from the hair while leaving it soft, detangled, and conditioned.

2. Description of the Prior Art

Along with the increase in the consciousness of hair-caring, in recent years, it is desired for hair-care toiletry compositions such as shampoos, rinses, hair treatments and the like to be excellent in the conditioning effects such as flexibility, smoothness, emollient effect, and the like in the hair after use. When the hair is washed with a soap, a synthetic wash, detergent and the like, excess fat is removed during washing. As a result, the hair loses smoothness, a dry and hard feeling is produced, the combing property is decreased, and broken hair or split hair may be produced. In order to eliminate these drawbacks, a hair care composition product, such as a shampoo or a rinse, contains ingredients that provide hair conditioning effects.

In addition to the above, many hair care products are not intended specifically for people of African descent. Persons of African descent typically have characteristics of dry and tightly coiled hair. Many hair creams currently on the market fail to loosen the curl pattern resulting in difficult comb-through, increased hair breakage due to styling stress, and decreased natural styling options. For the people of African descent, this is not an acceptable result.

SUMMARY

The present invention is a conditioning cleansing cream for removing oil and debris from the hair while leaving it soft, detangled, and conditioned. The conditioning cleansing cream comprises an amount of African Black Soap, an amount of Castor Oil, an amount of Aloe Vera Extract, an amount of Jojoba Oil, an amount of Coconut Oil, an amount of Rosemary extract, an amount of Shea Butter, and an amount of Glycerin.

In an embodiment of the present invention, the conditioning cleansing cream further includes an amount of Behentrimonium Methosulfate, an amount of either Cetearyl Alcohol or Vegetable Emulsifying Wax, and an amount of Citric Acid.

DETAILED DESCRIPTION OF THE PREFERRED EMBODIMENTS

The present invention is a conditioning cleansing cream, indicated generally at 10, for removing oil and debris from the hair while leaving it soft, detangled, and conditioned. While designed specifically for persons of African descent, the conditioning cleansing cream can be used by any person from any ethnic background.

The conditioning cleansing cream of the present invention is gentle for dry and tightly coiled hair, such as that characteristic of many people of African descent. The conditioning cleansing cream further temporarily loosens the curl pattern resulting in easier comb-thru, reduced hair breakage due to styling stress, and increased natural styling options. The conditioning cleansing cream is prepared with several ingredients (complete formulation below), including handmade African Black Soap from West Africa. Being a "true soap" according to the definition set forth by the FDA, i.e. a complex salt comprised solely of natural fats and saponifying agent(s), the ingredients for the African Black Soap are known to those persons skilled in the art and can include Cocos nucifera (Coconut Oil), butyrospermum parkii, (Raw Shea butter), Cocoa Pod ash, Water, Elaeis guineensis (Palm Kernel Oil). It should be noted that other ingredients can be included in African Black Soap. In many instances, the Black African Soap can be considered a standalone product in itself.

The unique properties of the conditioning cleansing cream of the present invention lie not only in the results produced by its use, but also in the formulation. The conditioning cleansing cream is comprised entirely of anhydrous ingredients, resulting in a self-preserving product with an indefinite shelf life. It is the first shampoo product of its kind to require no additional preservation to maintain the integrity and stability of the formula. This is very much in keeping with the current trend of high-end cosmetics, which are moving toward phosphate-free, sodium lauryl sulfate-free, and paraben-free formulations thereby creating an environmentally-friendly product.

The conditioning cleansing cream of the present invention is also unique in that it is both a retail product and raw material/base for cosmetics manufacturers. By manipulating the ratios of the ingredients in the formula, the conditioning cleansing cream assumes various consistencies, ideal not only for shampoo but for foaming/cream soap, body scrubs, and gentle surfactant additive in other soap formulations. The conditioning cleansing cream can be customized with an unlimited number of fragrance and color options, as well as cosmetic additives such as salts, clay, essential and fixed oils, additional conditioners and cosmetic actives, and exfoliants. Below is disclosed the formula and procedure for the basic conditioning cleansing cream. As understood by those persons skilled in the art, the percentages are adjustable to produce various consistencies and levels of viscosity depending on application.

Formula:
20% African Black Soap
14% Castor Oil
7% Behentrimonium Methosulfate
7% Cetearyl Alcohol (or Vegetable Emulsifying Wax)
2.5% Citric Acid
3% Aloe Vera
Extract
3% Jojoba Oil
3% Coconut Oil
3% Rosemary
extract
17.5% Shea Butter
20% Glycerin For skin applications, the above formula can also be adjusted by eliminating the pH adjuster Citric Acid and the conditioning ingredients Behentrimonium Methosulfate and Cetearyl Alcohol resulting in an all-natural formula (the latter two ingredients being naturally-derived chemicals).

Procedure:
1) All liquid oils (including aloe vera and rosemary extract) are warmed in a double boiler;
2) Behentrimonium Methosulfate and Cetearyl Alcohol (or vegetable emulsifying wax) are added and melted;
3) To this mixture, citric acid is added and agitated until dissolved. Set aside;
4) The African Black Soap is chopped into fine pieces using any common soap cutter;
5) The soap pieces are placed in an industrial high shear mixer;
6) Glycerin is added and mixed at high shear until the consistency of the soap is semi-liquid or gel;

7) Shea butter is added to the black soap and mixed at high shear until thoroughly incorporated. The color of the soap will lighten at this point due to the addition of Shea butter. (If fragrance or additives are used they can be incorporated at this stage.);
8) The warmed liquid oil mixture is now added to the soap, Shea butter, and glycerin; and
9) The ingredients are thoroughly mixed at high shear until a thick creamy paste-like texture is achieved.

The conditioning cleansing cream of the present invention is for the care of ethnic skin and hair, specifically African American, developed in response to a growing demand for quality natural hair care for persons of African descent. The formulation combines authentic African and Western ingredients for a unique cleanser and formulation base for the hair, the face, and the body. There is currently a tremendous demand from the high-end cosmetics users for gentle and effective cleansing products that are free from sodium lauryl sulfate, petrolatum byproducts, parabens, and other synthetic preservatives. As a result, the many home-based cosmetics formulators search for a base with the versatility to be integrated into face and body scrubs, liquid and cream cleansers, and shampoo. The conditioning cleansing cream of the present invention meets those specifications. It can be manufactured to several different consistencies and offered for sale to wholesale manufacturers, home crafters, small businesses, and retail customers. It can be customized with various fragrances, cosmetic additives, and packaging.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

What is claimed is:

1. A conditioning cleansing cream for removing oil and debris from the hair while leaving it soft, detangled, and conditioned, the conditioning cleansing cream comprising:
   an amount of African Black Soap;
   an amount of Castor Oil;
   an amount of Aloe Vera Extract;
   an amount of Jojoba Oil;
   an amount of Coconut Oil;
   an amount of Rosemary extract;
   an amount of Shea Butter; and
   an amount of Glycerin;
   wherein the amount of African Black Soap is approximately 20% of total volume, wherein the amount of Caster Oil is approximately 14% of total volume, wherein the amount of Aloe Vera Extract is approximately 2.5% of total volume, wherein the amount of Jojoba Oil is approximately 3% of total volume, wherein the amount of Coconut Oil is approximately 3% of total volume, wherein the amount of Rosemary Extract is approximately 3% of total volume, wherein the amount of Shea Butter is approximately 17.5% of total volume, and wherein the amount of Glycerin is approximately 20% of total volume.

2. The conditioning cleansing cream of claim 1 and further comprising:
   an amount of Behentrimonium Methosulfate;
   an amount of either Cetearyl Alcohol or Vegetable Emulsifying Wax; and
   an amount of Citric Acid.

3. The conditioning cleansing cream oil of claim 2 wherein the amount of Behentrimonium Methosulfate is approximately 7% of total volume, wherein the amount of Cetearyl Alcohol or Vegetable Emulsifying Wax is approximately 7% of total volume, and wherein the amount of Citric acid is approximately 2.5% of total volume.

4. The conditioning cleansing cream of claim 1 wherein the formulation is free from phosphate, free from sodium lauryl sulfate, and free from paraben.

5. The conditioning cleansing cream of claim 1 wherein the formulation is a self-preserving product.

6. The conditioning cleansing cream of claim 1 wherein the amount of each ingredient is varied thereby forming a substance selected from the group consisting of shampoo, foaming/cream soap, body scrubs, and surfactant additive in other soap formulations.

7. The conditioning cleansing cream of claim 1 and further comprising:
   an amount of salt.

8. The conditioning cleansing cream of claim 1 and further comprising:
   an amount of clay.

9. The conditioning cleansing creams of claim 1 and further comprising:
   an amount of essential and fixed oils.

* * * * *